United States Patent [19]

Dawson

[11] 4,379,139

[45] Apr. 5, 1983

[54] ANTICOAGULANT RODENTICIDE WITH LACERATION MEANS

[75] Inventor: Ray F. Dawson, Winter Park, Fla.

[73] Assignee: Lancaster Laboratories, Inc., Lancaster, Pa.

[21] Appl. No.: 285,607

[22] Filed: Jul. 21, 1981

[51] Int. Cl.³ .................... A01N 25/00; A01M 25/00; A01M 1/20

[52] U.S. Cl. ...................................... 424/84; 43/124; 43/131

[58] Field of Search ..................... 424/84; 43/124, 131

[56] References Cited

U.S. PATENT DOCUMENTS 2,783,177  2/1957  Link ..................................... 424/84
3,105,321 10/1963  Link .

FOREIGN PATENT DOCUMENTS 379356  8/1923  Fed. Rep. of Germany ........ 43/124

Primary Examiner—Delbert R. Phillips
Assistant Examiner—F. T. Moezie
Attorney, Agent, or Firm—Holman & Stern

[57] ABSTRACT

The invention incorporates a lacerating agent such as ground glass into a rodenticide composition which includes a bait and an anticoagulant. An additional edible attractant may be added to the foregoing components, serving additionally as a means to form aggregates of the other components in the shape of wafers or cakes.

21 Claims, No Drawings

ANTICOAGULANT RODENTICIDE WITH LACERATION MEANS

BACKGROUND OF THE INVENTION

1. Field of the Invention

The present invention is directed to rodenticide compositions. Specifically, the invention includes a mixture of an anticoagulant, a bait, and a laceration means.

2. Description of the Prior Art

The rodent problem has been recognized worldwide as a serious and age-old problem. In some underdeveloped areas of the world, rodents actively compete with man for available food supplies. In the more developed countries, rodents still manage to invade food warehouses, packing plants, slaughterhouses, food stores, farms, and fruit groves to cause substantial economic losses. When sufficiently hungry, and lacking other sources of food, they will in some cases, attack humans. They have also been known historically to be the carriers of a variety of diseases. Considering the magnitude and persistance of the problem, significant time and effort has been focused on numerous means and methods of resolving it.

Until the discovery of effective anticoagulants, most notable being warfarin, 3-($\alpha$-acetonlybenzyl) 4-hydroxycoumarin, numerous toxic methods have been employed. Such substances as arsenic, toxic and rapidly acting, single dose, stomach poisons such as strychnine or sodium fluoracetate have found widespread use. The use of these highly toxic materials has had significant drawbacks, however, since being so toxic, they provide a serious potential for accidental poisoning of humans, particularly children and domestic animals. Likewise, in the hands of non-professionals, some of these substances can be quite hazardous to those individuals dispensing the materials.

Studies have also indicated that some of the rapidly acting poisons frequently are rejected by a majority of the rodent colony. Such a response, known as "bait shyness", develops after toxic manifestations in several of the rodents are observed by the remaining rodents.

The introduction of anticoagulants, such as warfarin, into the rodenticide field, initiated a new and effective concept of multiple dose bait. When warfarin, or its sodium or potassium derivatives, are employed in small amounts with suitable baits, high kills of both rats and mice have been observed within a few days.

Since its commercial introduction in 1950, warfarin has been prepared and employed in a variety of compositions and forms. U.S. Pat. No. 2,783,177 describes the preparation of the sodium salt of warfarin which may be employed as a water bait. Aqueous solutions of the material may be coated on sand which may subsequently be placed in water, whereby the water soluble warfarin compound dissolves, the sand merely serving as a "carrier" for the rodenticide. U.S. Pat. No. 3,105,321, describes an anti-mouse board which appeals to the gnawing and destructive tendencies of a mouse, which unlike the rat, tends to chew or pick at their food, eating only small amounts at a particular time, but feeding often.

Warfarin, which at the time of its introduction was thought to be the most efficacious rodenticide, has in recent years proved to be less effective. Apparently, rodents have developed a resistance to the anticoagulent effect of warfarin. The exact mechanism for this resistance is not known, however, it is believed by some that if the organism can synthesize enough vitamin K, an anti-hemorrhagic compound, then the effects of anticoagulants are greatly reduced. Considering the competing effects, one approach to overcoming the resistance of organisms to anticoagulants has taken the form of combining the anticoagulant with sulfa drugs and/or an antibiotic. The belief was that such substances would reduce or eliminate intestinal flora which are responsible for synthesis of vitamin K. It was thought that this combination of components would potentiate or magnify the activity of the anticoagulent compound; however, such approaches have had only limited success in combating the resistance developed by rodents to anticoagulants. Thus, until the instant invention was developed, what once appeared to be the final solution to the rodent problem, seemed only to present a temporary holding action.

SUMMARY OF THE INVENTION

The present invention combines an anticoagulant, a bait, and a lacerating means. By including a lacerating means with the anticoagulant, when hemorrhaging fails to occur by natural means, it is induced by artificial means. Namely, once the rodent has ingested portions of the inventive compositions, internal tissue will be cut or lacerated and the anticoagulant will have a much more pronounced effect, even though the rodent may have developed a degree of resistance to such anticoagulants. Additionally, external bleeding may be induced by contact of the rodent with the lacerating means while walking over spilled material during a first or subsequent feeding. If desired, and according to a feature of this invention, the lacerating means may be somewhat disguised by coating the same with a material attractive to rodents.

DESCRIPTION OF THE PREFERRED EMBODIMENTS

The present invention contemplates a physical mixture of a rodenticide, a bait, and a lacerating means or agent. The exact manner in which these ingredients are combined and in what proportions will become clearer from the discussion which follows.

Any suitable anticoagulant may be employed in the present invention. Those which have found application as rodenticides are particularly preferred. This would also include the salts, commonly the alkali metal salts, of such compounds. Most preferably, warfarin or 3-($\alpha$-acetonylbenzyl)-4-hydroxycoumarin or its metal salts are employed.

Any hard substance having jagged edges or edges with acute angles of any suitable shape and size capable of cutting, lacerating, or otherwise severing tissue is suitable as a lacerating agent in the present invention. This would include such things as broken glass, shredded metal, steel wool, metal filings or powder, glass wool of short fiber length, ceramic fragments or fibers, naturally occurring materials such as hard nut shells, bone fragments, volcanic glass, such as pumice, and any other suitable hard and often discarded material is also suitable for use in the present invention. The most preferred product, however, is broken or crushed glass of almost any type. It is preferred both because it has been proven effective as well as its low cost.

Particle size does not appear to be one of the more critical features. It should be of such a size as to be easily ingested by the rodent along with the edible bait.

Those rodents which tend to take smaller bites and pick at their food, such as mice, require smaller particle sizes. A suitable size range would include those particles having diameters on the order of about 0.1 to 5 millimeters. A preferred range would include those particles having diameters of approximately 0.5 to 3 millimeters.

Suitable baits would include anything which could serve as an attractant to a rodent. The only limitation is that the material not deteriorate with age or exposure to a variety of climatic conditions if it is to be prepackaged or stored for a long period of time. The material should also be capable of blending or mixing physically with the rodenticide and without reaction therewith. Such baits should, preferably, be solid after processing is complete, particularly if it is to be prepackaged. Suitable baits would include edible grain products such as whole, cracked, or extruded grains or cereals, pelletized raw garbage, shredded sugar cane, dehydrated waste banana pulp, tankage and/or meat scrap, dehydrated canning waste, and cheese whey. Although some of these baits are considered general purpose baits, that is, being suitable for use in a variety of different situations and conditions, some of the afore-mentioned materials are more suited to those environments in which the same or similar substances may be found. The shredded sugar cane or dehydrated waste banana pulp, for instance, may be used in cane fields, banana plantations, or fruit orchards or groves generally. The most preferred bait, however, includes the whole, cracked, crushed, puffed or popped grains or cereals.

The several components of the present invention may be combined in a variety of ways. In most of the embodiments of the present invention, the anticoagulant will be mixed or blended with the bait and the mixture subsequently combined with the lacerating agent. Thus, in the first step, the anticoagulant rodenticide may be sprayed onto the bait, either neat if the anticoagulant is a liquid, or in solution. Alternatively, the two materials may simply be combined and thoroughly stirred or agitated. In the situation in which the bait is a solid, the anticoagulant forms a coating which may or may not be absorbed by the bait depending upon the surface or porous character of the bait. If the bait is in a very fine state of subdivision, the anticoagulant and bait may be intimately mixed. In the case of extruded or pelletized grain products, as an alternative to coating the pellets produced thereby, the grain and anticoagulant may be thoroughly mixed prior to extrusion or pelletization. The commercially available rodenticide composition known as d-CON (a trademark of the d-CON Company, Inc., a subsidiary of Sterling Drug Company, Inc.) which is available as either a cracked or extruded grain product containing warfarin, provides a preferred combination of bait and anticoagulant. Once formed, the bait-anticoagulant combination is subsequently mixed with the lacerating agent by any suitable mechanical method which assures uniform blending. The components should be sufficiently mixed to eliminate stratification or concentration gradients of the lacerating agent.

A suitable concentration of anticoagulant would lie within the range of 0.005% to 2.0% by weight. A preferred range of the anticoagulant would be approximately 0.01% to 1.25% by weight. A suitable range of concentration of the lacerating agent would be from about 5 to 60% by weight; the preferred range being from approximately 15 to 50% by weight. The bait would be present in the instant invention in a range from 40 to 95% by weight, with a preferred range of approximately 50 to 85% by weight. The above materials would vary widely in their concentrations depending upon the shapes, particle sizes and densities of the various components. Thus, were metal filings to be employed, rather than ground glass as the lacerating agent, while the two materials might be present in the same percentage by volume, the metal shavings would be present in a much higher percentage by weight.

The present invention also contemplates embodiments which are somewhat different than those described above. Namely, in addition to the above described 3 components, a fourth is added which may serve as a supplemental attractant to the bait and/or a binder or edible adhesive. Thus, to the above listed ingredients may be added a syrup derived from one or more carbohydrates such as dextrins, polysaccharides, carmelized carbohydrates, or combinations of the foregoing.

In this embodiment any manner of mixing which achieves uniform coating of the lacerating agent and bait by the binder is suitable. Thus, the lacerating agent, bait, and anticoagulant may be mixed as set forth above and the edible binder subsequently added to the mixture with agitation. Alternatively, the bait and lacerating agent may be coated separately, the former after it has been coated with or combined with anticoagulant. In the above methods of mixing, the binding agent is combined with the other components as a liquid, either neat or in solution. In still another variant, a solution of the binding agent and anticoagulant may be formed which is subsequently mixed with the lacerating agent and the bait, separately or as a mixture.

Dependant upon such factors as the order and manner of mixing the other components with the edible binder (that is, separately or combined), the moisture content of the binder, viscosity of the syrup, temperature and such other factors which are within the purview of the skilled artisan, individual coated particles of bait and lacerating agent may be formed or mixed aggregates in the form of cakes or wafers can be obtained.

Cakes or wafers of the bound mixture may be formed while the binder is still moist by suitable molding or pressing techniques. Alternatively, sheets of the bound mixture may be formed which after drying and hardening, may be cut or broken into smaller portions. A preferred combination of ingredients in the cake or wafer form of the invention would include warfarin, ground glass, popped corn, and carmelized carbohydrates or corn syrup or a mixture of the last two mentioned components.

In the aggregate embodiment of the invention, the concentrations would be those set forth above for the suitable and preferred concentrations for lacerating agents, anticoagulant, and bait and suitably include 1 to 25% by weight of the edible binder. The latter component would be present in a preferred range of from approximately 2.5% to 20% by weight.

According to a feature of this invention, the lacerating agent may be somewhat disguised from the rodents, encouraging the ingestion of the mixture. For example, a polysaccharide, such as a sugar solution can be carmelized in any conventional manner, such as by boiling, and then uniformly blended with the lacerating agent, such as ground glass, to coat the lacerating agent. Then the coated lacerating agent may be blended as before with a bait/anticoagulant material to produce the final product. Care should be taken in coating the lacerating agent to insure that the sharp edges remain after coating. Thus, a relatively thin coating should be used. Further, since the primary purpose of this embodiment is to improve the likelihood of ingestion of the lacerating agent, a significant proportion of lacerating agent of smaller particle sizes within the range specified above would be most applicable in the production of such a material.

EXAMPLE

Two pounds of a commercially available mixture of warfarin and a cracked whole grain product, d-CON, were mixed with approximately 0.9 pounds of crushed glass prepared by crushing a 10-ounce (by volume) beverage container. The components were mixed such that it would be difficult for rats to consume the bait without consuming at least some of the powdered glass. Further, were the rats successful in spilling the mixture, it was felt that lacerations would be induced as the rodents walked over the scattered mixture.

The mixture was placed in metal cans having plastic lids sealed to their openings. A small hole, approximately 1.5 inches in diameter, was cut in the plastic lid. The size of the hole was selected in order to allow rats to feed or admission to the can but to prevent squirrels from feeding on the mixture. The containers were secured with screws to stakes and the latter driven into the soil to prevent wastage by larger rodents. The containers were placed in and near a citrus grove along runways known to be frequented by rats, near compost heaps and around fire place wood piles.

The rodenticide mixture was consumed avidly for about one week after the dispensers were set out. During this period, the mixture was replenished as required. A nighttime rain terminated this one week period and on the following morning, dead rats were found in areas surrounding the dispensers.

Consumption of the bait continued for a period of approximately two weeks thereafter at a much reduced rate. It then terminated suddenly and no detectable additional consumption occurred during the next 2.5 months, although the composition was readily available. Damage to citrus fruits ceased completely after the first sighting of dead rats and no damage occurred during the following 2.5 months.

The same composition as above, but without the lacerating means of this invention, had been previously used in a similar manner in the same citrus grove without significant success in reducing the rat population or diminishing damage to the citrus fruits.

While in the foregoing specification a detailed description of the present invention has been set forth including reference to specific embodiments, this is for the purpose of illustration and is not intended to limit in any way the present invention. Thus, without departing from the spirit and scope of the instant invention, alternate and additional components and modifications may be made to the above described embodiments as would be apparent to those skilled in the art. This would include alternate and additional anticoagulants, lacerating agents, attractants or baits and the so called potentiating agents such as sulfa drugs and/or antibiotics generally.

What is claimed is:

1. A rodenticide composition consisting essentially of an anticoagulant present in a concentration of at least about 0.005% by weight, based on the weight of the total rodenticide composition, an edible bait and a lacerating agent present in a concentration of at least about 5% by weight, based on the weight of the total rodenticide composition.

2. A rodenticide composition according to claim 1, wherein said anticoagulant is warfarin.

3. A rodenticide composition according to claim 1, wherein said edible bait is selected from the group consisting of edible grain products, cereals, pelletized raw garbage, shredded sugar cane, dehydrated waste banana pulp, dehydrated canning waste, cheese whey, tankage scraps and meat scraps.

4. A rodenticide composition according to claim 1, wherein said edible bait is an edible grain product.

5. A rodenticide composition according to claim 1, wherein said lacerating agent is selected from the group consisting of broken or powdered glass, glass wool, pumice, metal filings, steel wool, ceramic fragments, bone fragments, and hard nut shells.

6. A rodenticide composition according to claim 1, wherein said lacerating agent is broken or ground glass.

7. A rodenticide composition according to claim 1, consisting essentially of warfarin, a grain or grain product and broken glass.

8. A rodenticide composition according to claim 1, additionally including an edible binder.

9. A rodenticide composition according to claim 8, wherein said edible binder is a carbohydrate.

10. A rodenticide composition according to claim 8, wherein said rodenticide composition is formed into cakes or wafers.

11. A rodenticide composition according to claim 8, wherein said bait is popped corn.

12. A rodenticide composition according to claim 8, comprising cakes or wafers of warfarin, popped corn, a carbohydrate binder and broken glass.

13. A rodenticide composition according to claim 1, consisting essentially of particles of glass having sharp edges coated with a carmelized polysaccharide in admixture with said anticoagulant and bait.

14. A rodenticide composition according to claim 1, wherein said anticoagulant is present in amounts between 0.005% to 2.0% by weight, based on the weight of the total rodenticide composition.

15. A rodenticide composition according to claim 1, wherein said anticoagulant is present in amounts between 0.01% to 1.25% by weight, based on the weight of the total rodenticide composition.

16. A rodenticide composition according to claim 1, wherein said lacerating agent is present in amounts between 5% to 60% by weight, based on the weight of the total rodenticide composition.

17. A rodenticide composition according to claim 1, wherein said lacerating agent is present in amounts between 15% to 50% by weight, based on the weight of the total rodenticide composition.

18. A rodenticide composition according to claim 1, wherein said edible bait is present in amounts between 40% to 95% by weight, based on the weight of the total rodenticide composition.

19. A rodenticide composition according to claim 1, wherein said edible bait is present in amounts between 50% to 85% by weight, based on the weight of the total rodenticide composition.

20. A rodenticide composition according to claim 8, wherein said edible binder is present in amounts between 1% to 25% by weight, based on the weight of the total rodenticide composition.

21. A rodenticide composition according to claim 8, wherein said edible binder is present in amounts between 2.5% to 20% by weight, based on the weight of the total rodenticide composition.

* * * * *